United States Patent [19]
Gatenholm

[11] Patent Number: 6,020,278
[45] Date of Patent: Feb. 1, 2000

[54] METHOD FOR THE PRODUCTION OF HIGHLY ABSORBENT HYBRID FIBERS BY OZONING AND GRAFT POLYMERIZING AND HYBRID FIBERS PRODUCED THROUGH THE METHOD

[76] Inventor: Paul Gatenholm, Sodra Fjarskogsvagen 23, Onsala, Sweden, S-439 33

[21] Appl. No.: 09/091,075
[22] PCT Filed: Nov. 25, 1996
[86] PCT No.: PCT/SE96/01529
  § 371 Date: Nov. 24, 1998
  § 102(e) Date: Nov. 24, 1998
[87] PCT Pub. No.: WO97/22744
  PCT Pub. Date: Jun. 26, 1997

[30] Foreign Application Priority Data

Dec. 15, 1995 [SE] Sweden .................................. 9504496

[51] Int. Cl.[7] .......................... D06M 14/00; D06M 11/34
[52] U.S. Cl. .......................... 442/414; 442/327; 525/242
[58] Field of Search ............................ 525/242; 442/414, 442/327

[56] References Cited

U.S. PATENT DOCUMENTS 3,656,884  4/1972  Okaya et al. ............................. 8/116.1

FOREIGN PATENT DOCUMENTS 55036334  8/1978  Japan .
7051565  8/1993  Japan .
7090774  9/1993  Japan .

OTHER PUBLICATIONS

J.P. 7051565 Abst, Aug. 1993.
J.P. 7090774 Abst, Sep. 1993.
J.P. 55036334 Abst, Aug. 1978.

*Primary Examiner*—Daniel Zirker
*Attorney, Agent, or Firm*—John S. Munday

[57] ABSTRACT

The invention relates to a method for the production of highly absorbent or superabsorbent hybrid fibers by ozoning of natural or synthetic fibers and subsequent graft polymerizing on the ozoned fibers. The method is characterized in that the ozoned fiber is graft polymerized in a water solution, containing ionizable or swellable monomers having hydrophilic groups and cross-binders comprising polyfunctional groups. The invention also comprises a product produced by the method according to the invention.

18 Claims, No Drawings

METHOD FOR THE PRODUCTION OF HIGHLY ABSORBENT HYBRID FIBERS BY OZONING AND GRAFT POLYMERIZING AND HYBRID FIBERS PRODUCED THROUGH THE METHOD

FIELD OF THE INVENTION

The present invention relates to a method for the production of high absorbent or superabsorbent hybrid fibres by ozoning of natural or synthetic fibres and subsequent graft polymerizing on the ozoned fibres and a product produced through the method.

PRIOR ART

It is known to modify the surface of a fibre so that it is provided with reactive groups and thereafter to bind monomers or polymers to these groups by so-called graft polymerization. In this way, the fibres may be given new and desirable properties of different kinds depending on the degree of change of the surface of fibre or its length and the kind and amount of the polymers which have been grafted thereon.

Two methods are especially known for modifying the fibre, namely irradiating with UV light or radioactive rays, especially gamma rays, electron rays (EB=electron beam) and the like, or oxidation of the surface with organic peroxides or ozone. The chemical theory for the creation of these reactive groups is well-known and is not further discussed here.

When modifying the surface, the polymer molecules are also cut to some extent and reactive groups are created on the surface. A great number of monomers of different kinds can therefore be bound to these reactive groups and the polymer molecules can also be coupled to each other again, optionally via some monomer or polymer.

An example of graft polymerization of synthetic fibres is disclosed in the Japanese patent publication 7 090 774 which describes graft polymerization by means of irradiation. After polymerization which is carried out with an acid group containing vinyl monomers, such as methacrylic acid, the fibre is treated with alkali and a hydrophilic compound. Good water absorption and excellent washing properties are thus obtained.

Another example of graft polymerization is disclosed in the Japanese patent publication 7 051 565 in which melt spun synthetic fibres are graft polymerized with epoxy groups containing monomers whereupon the fibres are reacted with triazine or a melamine compound and thereafter heat-treated under humid conditions. The activation of the fibre is brought about by radioactive irradiation, with an organic peroxide or ozone. These fibres obtain the property that they do not melt so easily.

A futher example of graft polymerization is disclosed in the Japanese patent publication 55 03 63 34 which describes graft polymerization of natural protein fibres such as wool and silk in which the modification of the fibre occurs by electron beams, peroxides, ozone or UV rays. The polymer which is used is a styrene derivate and the fibres are given better properties in relation to colouring, washing, pressing, flexibility, resistence against chemicals, etc without any negative influence on the inherent properties of the fibres.

TECHNICAL PROBLEM

It has long been a desire to improve the water absorption ability of natural or synthetic fibres so that they become highly absorbent or superabsorbent. Absorbent fibres, especially based on cellulose, are desirable and used in many different occasions, especially in napkins, incontinence protection, etc. Very high demands are made in the case of such use on the absorption ability and on the way in which the absorption is carried out, as well as on the product after the absorption has been carried out so that no feeling of wetness is observed. To increase the absorption ability and make it sufficient in such hygienic contexts, granules or powder have therefore been added to the cellulose mass, which granules or powder are superabsorbent, which means that they can absorb up to a hundred times their own weight of water. A problem with these superabsorbents is, however, that they firstly must be added in a separate step during the production, and secondly that they must be maintained in place in the finished product during use, which creates a great difficulty. It has therefore long been a desire to be able to avoid these added superabsorbents and instead make the absorbent fibre mass so highly absorbent that it suffices for use in hygienic products.

THE SOLUTION

According to the present invention, the above problem has been solved and a process for the production of highly absorbent or superabsorbent hybrid fibres has been brought about by ozoning natural or synthetic fibres and subsequent graft polymerizing on the ozone fibre, which method is characterized in that the ozoned fibre is graft polymerized in a water solution containing ionizable and swellable monomers having hydrophilic groups and cross-binders including polyfunctional groups.

The fibres which preferably are used according to the invention are cellulose fibres in the form of paper pulp, paper, fluff, non-woven, regenerated fibres (continuous or staple fibres) or long vegetable fibres such as cotton, jute, flax or synthetic fibres such as polypropene, polyethene, polyester or polyacryl.

According to the present invention the ozoning can be carried out with an ozone gas mixture which is saturated with water or in a water solution.

The ozoning is preferably carried out at a temperature of in the region of 15–50° C. during a period of time which lasts up to 90 minutes.

According to the invention, the ionizable monomer consists preferably of acrylic acid, methacrylic acid, sodium salts thereof, hydroxyethyl methacrylate, diethylene glycol methacrylate, acrylamide, methacrylamide, vinyl pyrrolidone or mixtures thereof.

The cross-binder which is used according to the invention consists suitably of diethylene glycol methacrylate (DEGMA), triethylene glycol dimethacrylate (TEDGMA), N,N-methylene bis-acrylamide (MBAAm), ethylene-bis-vinylpyrrolidone (EBVP) or mixtures thereof.

The graft polymerization is suitably carried out in a water solution which also contains 0,05–0,6% of Mohr salt $(FeSO_4.(NH_4)_2SO_4.6H_2O)$ of the monomer.

According to the present invention, the graft polymerization should occur at a pH of between 1 and 3 and at a temperature of 50–60° C. during a period of time of 10–180 minutes.

According to the invention, it is suitable that the cross-binder is present in an amount of up to 20 weight % of the monomer.

The invention also comprises a product produced by the method according to the present invention.

DETAILED DESCRIPTION

The ozoning of, for example, cellulose is an oxidation process of hydroxyl groups where hydroperoxides are formed. According to the invention, this ozoning is carried out in the presence of water, preferably in the form of steam in an ozone gas mixture saturated with water vapour. This mixture may, besides containing water vapour to a maximal degree, consist of oxygen gas which has passed a lightning discharge chamber or of air which has passed the same chamber or which has been admixed with ozone. The temperature during the ozoning should be kept in the region of 15–50° and a through flow of the fibre mass with the ozone gas mixture can then suitably occur during a period of time of up to 90 minutes. Neither the temperature nor the time is critical in this connection but these parameters may be varied as wished so that a desired degree of ozonisation can be obtained. It is also possible to immerse the fibre mass in a water solution and let the ozoning occur therein by through flowing of ozone containing gas while stirring so that the fibre mass will come into contact with the ozone.

The ozoning is, as stated above, an oxidation process of hydroxyl groups where hydroperoxides are formed. When cellulose is ozoned with humid ozone or in a water solution, it is supposed that the water swells the cellulose and makes it more accessible for the chemical reactions. A part of the ozone also reacts with the water whereby hydroxyl radicals are formed.

Besides the peroxide production the ozone also contributes to degradation of the cellulose. This degradation deteriorates the mechanical properties, but these can be sustained by a subsequent grafting.

When peroxides are formed on the surface, the graft polymerization can be carried out. One condition is, however, that oxygen is carefully removed as well as possible inhibitors which, for example, may be stabilizers in the monomer but also certain metals, for example, copper.

The amount of synthetic polymer which is grafted on the cellulose depends on several factors of which the ozoning time, the monomer concentration and the grafting time, the temperature and the amount of cross-binders are the most important.

The duration time between ozoning and grafting is also of importance when as high a concentration of hydroperoxides as possible is wanted on the surface of the substrate. A thermal decomposition of hydroperoxides in the presence of the monomers which are to be grafted on the cellulose chain promotes the homopolymerization since it provides hydroxyl radicals which are more mobile than the macro-radicals.

By the addition of $Fe_2$ ions (Mohr salt) the decomposition of hydroperoxides can be conducted in such a way that the homopolymerization reaction is eliminated.

The monomers which should be used according to the present invention are water soluable and after polymerization form hydro gels together with water. Preferred monomers are hydroxyethyl methacrylate (HEMA) and also diethylene glycol methacrylate (DEGMA):

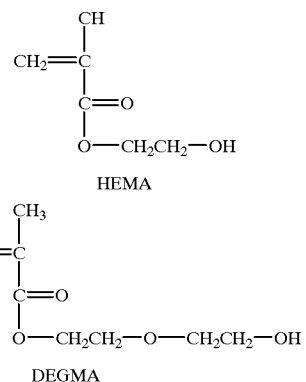

The ionizable monomer can, as stated above, also be acrylic acid, methacrylic acid, sodium salts thereof, hydroxyethyl methacrylate, diethylene glycol methacrylate, acrylamide, methacrylamide, vinyl pyrrolidone, mixtures thereof or other suitable monomers.

In order for the fibres to obtain the very high water absorbing effect, it is necessary that the grafted polymer chains are cross-bound so that a network is obtained. One or more cross-binders are therefore also added to the polymer mixture. Such a cross-binder is preferably diethylene glycol dimethacrylate which is a bifunctional monomer (DEGDMA):

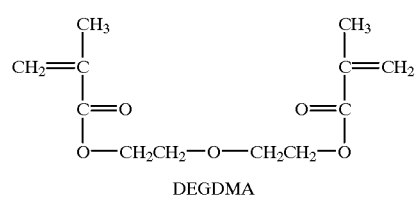

Also other cross-binders such as N,N-methylene bis-acrylamide, ethylene-bis-vinylpyrrolidone, ethyldimethacrylate, triethylene glycol dimethacrylate or mixtures thereof or other cross-binders may be used.

The solvent in the monomer solution is suitably 50% water and 50% methanol. An example of a monomer solution is 3,0 gram monomers having a determined content of cross-binders which is admixed with 15 ml methanol followed by 15 ml Mohr salt solution (5 gram/liter water). To regulate the solution, nitrogen is bubbled through it during 5 minutes whereupon pH is adjusted to 3,0 with HCl followed by further bubbling with nitrogen during 20 minutes. This occurs for a monomer such as HEMA. When only acrylic acid is used the solvent consists suitably of only water and the monomer can preferably be present in a concentration of about 30 weight %.

The graft polymerization was carried out in a polymerization receptacle in which the ozoned fibres had been placed whereupon the receptable had been closed. The receptacle was thereafter evacuated and filled with nitrogen three times in succession to remove all oxygen and was thereafter placed in an agitated water bath with a temperature of 50° C. After 60 minutes the samples were taken up and rinsed in methanol whereupon they were laid down in methanol and extracted overnight at 20° C. in an agitated water bath to remove all possible homopolymers.

EXAMPLE 1

Sheets of cellulose fibres in the form of cotton linters (Munktell filter paper no. 5) were placed in an ozone reactor and exposed during 90 minutes to ozone/oxygen gas with a gas flow of 250 liters/hour and an ozone concentration av 25 grams/m$^3$. The ozoned material was then treated with nitrogen gas during 5 minutes and placed thereafter in a water solution containing 30% acrylic acid, 6% N,N-bis-acrylamide and 0,3% Mohr salt. In the solution the pH was maintained at 1,5. After agitation during 30 minutes at 50° C., the cellulose sample was washed and weighed. The material contained 500% polyacrylic acid. This amount of polyacrylic acid means that the fibre material has increased its weight 5 times through the addition of grafted polyacrylic acid.

Accordingly, the fibres treated in this way contain a covalent bound (grafted polymer) which in water forms a hydro gel and creates accordingly a swelling of the material. Moreover, the swelling is promoted when the fibre material is aftertreated with alkali and/or acid.

EXAMPLE 2

Non-woven-fibre of polypropene was placed in an ozone reactor, and exposed during 45 minutes as described in example 1.

The ozoned fibre was thereafter grafted in a solution of 30% acrylic acid, 10% EDMA and 0,3 weight % of Mohr salt based on the monomer. After 25 minutes the grafting was visible. After 100 minutes the material contained 1800% polyacrylic acid. This means that the fibre material had increased its weight by 18 times. The fibres were thereafter treated with 1M NaOH at 80° C. during 3 hours and were dried.

When the fibres were placed in water they absorbed water at an amount of 75 times their own weight in 5 minutes.

Through the present invention it is accordingly possible to produce a superabsorbent which is defined in that it has capacity to absorb large quantities of liquid. In practice, this is possible if the material remains insoluble in the liquid which it absorbs. An important difference between a synthetic superabsorbent and a conventional absorbent such as fluff mass is that a superabsorbent has the ability to hold the liquid under pressure.

A superabsorbent according to the present invention comprises cross-bound chains of a very hydrophilic polymer. The cross-binder influences the chain transmission and gives greater grafting yield. This is of importance if the process is intended to be applied during short periods on an industrial scale. Cross-binders also create cross-binding between grafted chains. The density of the cross-bindings influences both the swelling ability and the ability to hold the liquid under pressure.

According to the present invention, an effective and cheap method for the production of high absorbent or superabsorbent hybrid fibres has accordingly been obtained. The method can easily be continuous in a cellulose bleaching plant where ozone is already used for bleaching fibres. The pulp which is to be used for forming the superabsorbent hybrid fibres can then in a first step be ozoned according to the present invention and then directly after the ozoning be graft polymerized and cross-bound and after-treated with alkali and/or acid in a continuous process without any large investment costs. A material is thereby obtained which is directly suitable for liquid absorption in napkins, incontinence protection, etc. without any addition of other superabsorbents.

The invention is not limited to the above-mentioned embodiment but can be varied in different ways within the scope of the claims. Thus, it may be applied on membranes as well as on fibres. Accordingly, the expression fibres in claims and description also comprises membranes.

I claim:

1. A method for the production of high absorbent hybrid fibers, comprising the steps of:
   ozoning fibers selected from the group consisting of natural and synthetic fibers to produce ozoned fibers; and
   subsequently graft polymerizing said ozoned fibers in a water solution containing ionizable and swellable monomers with hydrophilic groups and cross-binders comprising polyfunctional groups.

2. The method of claim 1, wherein said fibers are selected from the group of paper pulp, paper, fluff, non-woven, continuous or stable regenerated fibers, long vegetable fibers selected from the group consisting of cotton, jute, and flax, polypropylene, polyethylene, polyester and polyacrylates.

3. The method of claim 1, wherein said ozoning is carried out with an ozone gas mixture which is saturated with water or is in a water solution.

4. The method of claim 1, wherein said ozoning is carried out at a temperature ranging from 15° to 60° C. during a period of time of up to 90 minutes.

5. The method of claim 1, wherein said ionizable monomer is selected from the group consisting of acrylic acid and sodium salts thereof, methacrylic acid and sodium salts thereof, hydroxyethlyl methacrylate, diethylene glycol methacrylate, acrylamide, methacrylamide, vinyl pyrrolidone and mixtures thereof.

6. The method of claim 1, wherein said cross-binder is selected from the group consisting of diethylene glycol methacrylate, triethylene glycol dimethacrylate, N,N-methylene-bis-acrylamide, ethylene-bis-vinylprrolidone, ethylene dimethacrylate and mixtures thereof.

7. The method of claim 1, wherein said graft polymerization occurs in a water solution containing 0.05% to 0.06% of Mohr salt, based on the weight of the monomer.

8. The method of claim 1, wherein said graft polymerization is carried out at a pH ranging from 1 to 3 and at a temperature ranging from 50° to 60° C. during a period of time of up to 10 to 180 minutes.

9. The method of claim 1, wherein said cross-binder comprises about 1% to about 20%, based on the weight of said monomer.

10. A high absorbent hybrid, comprising:
    ozoned fibers selected from the group consisting of natural and synthetic fibers which have subsequently been graft polymerized in a water solution containing ionizable and swellable monomers with hydrophilic groups and cross-binders comprising polyfunctional groups.

11. The fibers of claim 10, wherein said fibers are selected from the group of paper pulp, paper, fluff, non-woven, continuous or stable regenerated fibers, long vegetable fibers selected from the group consisting of cotton, jute, and flax, polypropylene, polyethylene, polyester and polyacrylates.

12. The fibers of claim 10, wherein said ozoning is carried out with an ozone gas mixture which is saturated with water or is in a water solution.

13. The fibers of claim 10, wherein said ozoning is carried out at a temperature ranging from 15° to 60° C. during a period of time of up to 90 minutes.

14. The fibers of claim 10, wherein said ionizable monomer is selected from the group consisting of acrylic acid and sodium salts thereof, methacrylic acid and sodium salts thereof, hydroxyethlyl methacrylate, diethylene glycol methacrylate, acrylamide, methacrylamide, vinyl pyrrolidone and mixtures thereof.

15. The fibers of claim 10, wherein said cross-binder is selected from the group consisting of diethylene glycol methacrylate, triethylene glycol dimethacrylate, N,N-methylene-bis-acrylamide, ethylene-bis-vinylprrolidone, ethylene dimethacrylate and mixtures thereof.

16. The fibers of claim 10, wherein said graft polymerization occurs in a water solution containing 0.05% to 0.06% of Mohr salt, based on the weight of the monomer.

17. The fibers of claim 10, wherein said graft polymerization is carried out at a pH ranging from 1 to 3 and at a temperature ranging from 50° to 60° C. during a period of time of up to 10 to 180 minutes.

18. The fibers of claim 10, wherein said cross-binder comprises about 1% to about 20%, based on the weight of said monomer.

* * * * *